US009044500B2

(12) United States Patent
Kawa et al.

(10) Patent No.: US 9,044,500 B2
(45) Date of Patent: Jun. 2, 2015

(54) COMPOSITION FOR XEROSTOMIA

(75) Inventors: Gertrud Kawa, Buehl (DE); Shireen Uppal, Weybridge (GB); David Urquhart, Weybridge (GB)

(73) Assignees: GlaxoSmithKline Consumer Healthcare GmbH & Co KG, Buehl (DE); Glaxo Group Limited, Greenford (GB)

( * ) Notice: Subject to any disclaimer, the term of this patent is extended or adjusted under 35 U.S.C. 154(b) by 971 days.

(21) Appl. No.: 11/572,751

(22) PCT Filed: Jul. 29, 2005

(86) PCT No.: PCT/EP2005/008327
§ 371 (c)(1),
(2), (4) Date: Aug. 15, 2008

(87) PCT Pub. No.: WO2006/013081
PCT Pub. Date: Feb. 9, 2006

(65) Prior Publication Data
US 2008/0317703 A1     Dec. 25, 2008

(30) Foreign Application Priority Data

Aug. 2, 2004   (GB) .................................. 0417193.0
Feb. 1, 2005   (GB) .................................. 0502077.1

(51) Int. Cl.
| | | |
|---|---|---|
| A61K 8/00 | (2006.01) |
| A61K 31/79 | (2006.01) |
| A61K 8/73 | (2006.01) |
| A61K 8/81 | (2006.01) |
| A61Q 11/00 | (2006.01) |

(52) U.S. Cl.
CPC . *A61K 31/79* (2013.01); *A61K 8/73* (2013.01); *A61K 8/731* (2013.01); *A61K 8/8176* (2013.01); *A61K 8/8182* (2013.01); *A61Q 11/00* (2013.01)

(58) Field of Classification Search
USPC .......................................................... 424/49
See application file for complete search history.

(56) References Cited

U.S. PATENT DOCUMENTS

| | | | |
|---|---|---|---|
| 4,292,299 | A | 9/1981 | Suzuki et al. |
| 5,496,558 | A | 3/1996 | Napolitano et al. |
| 5,541,165 | A | 7/1996 | Turgeon et al. |
| 5,612,207 | A | 3/1997 | Nicolau et al. |
| 5,886,054 | A | 3/1999 | Van Nieuw Amerongen et al. |
| 5,900,247 | A | 5/1999 | Rault et al. |
| 6,210,699 | B1 * | 4/2001 | Acharya et al. ............... 424/435 |
| 6,585,997 | B2 * | 7/2003 | Moro et al. .................... 424/434 |
| 2001/0022964 | A1 | 9/2001 | Leung et al. |
| 2002/0168334 | A1 | 11/2002 | Jacob et al. |
| 2003/0060486 | A1 | 3/2003 | Jacob et al. |
| 2003/0124065 | A1 * | 7/2003 | Majeti et al. .................... 424/49 |
| 2003/0206941 | A1 * | 11/2003 | Leung et al. .................... 424/443 |
| 2004/0062724 | A1 | 4/2004 | Moro et al. |
| 2004/0071755 | A1 * | 4/2004 | Fox .................................. 424/443 |

FOREIGN PATENT DOCUMENTS

| | | |
|---|---|---|
| CA | 2504488 | 6/2004 |
| EP | 0452268 A2 | 10/1991 |
| EP | 0691124 A1 | 10/1996 |
| EP | 0781550 A | 7/1997 |
| EP | 1334710 A | 8/2003 |
| GB | 2194145 A | 3/1988 |
| JP | 60 215622 A | 10/1985 |
| JP | 61 017510 A | 1/1986 |
| JP | 03 034928 A | 2/1991 |
| JP | 03034928 A * | 2/1991 |
| JP | 5262629 | 10/1993 |
| WO | WO92/03124 A | 3/1992 |
| WO | WO97/00665 A | 1/1997 |
| WO | 9915210 | 4/1999 |
| WO | WO00/59423 A | 10/2000 |
| WO | WO03/015748 A | 2/2003 |
| WO | 2004000252 A1 | 12/2003 |

OTHER PUBLICATIONS

Patent Abstract of Japan vol. 010, No. 166 (C-353) (Jun. 13, 1986).
Patent Abstract of Japan vol. 010, No. 078 (C-335) (Mar. 27, 1986).
Patent Abstracts of Japan vol. 015, No. 163 (C-0826) (Apr. 24, 1991).
Patent Abstracts of Japan, Publication No. 2004-136102, 1 page, (May 13, 2004).
Patent Abstracts of Japan, Publication No. 08-333226, 1 page, (Dec. 17, 1996).
Patent Abstracts of Japan, Publication No. 63-179823, 1 page, (Jul. 23, 1988).
Patent Abstracts of Japan, Publication No. 05-058866, 1 page, (Mar. 9, 1993).
Patent Abstracts of Japan, Publication No. 07-010757, 1 page, (Jan. 13, 1995).
Partial Translation of JP Patent, Publication No. 2004-136102, 2 pages.
Japanese Examiner Shinsuke Aramaki, Notice of Reasons for Rejection Patent Application No. 2007-524259, 4 pages, (Sep. 5, 2011).
IP Australia Examiner Thomas Case, Examiner's First Report on Patent Application No. 2005268926, 2 pages, (Feb. 1, 2010).
EPO Examiner T. Donovan-Beermann, EPO Office Action 05 766 797.4, 4 pages, (Aug. 3, 2007).
Partial Translation of JP Patent, Publication No. 8-333226, 2 pages.
WIPO Officer Ellen Moyse, International Preliminary Report on Patentability for International Application No. PCT/EP2005/008327, 8 pages, (Feb. 6, 2007).
WIPO Officer Donovan-Beermann, T., International Search Report for International Application No. PCT/EP2005/008327, 4 pages, (Oct. 25, 2005).
CIPO Examiner Philip O. Brown, Ph.D., Office Action 2,575,605, 2 pages, (Oct. 15, 2012).
CIPO Examiner Philip O. Brown, Ph.D., Office Action 2,575,605, 4 pages, (Oct. 12, 2011).
Milligan, Adam C., "Office Action for Patent Application No. 13932088", Mailed Date: Oct. 9, 2014, 7 pages.

* cited by examiner

*Primary Examiner* — Adam C Milligan

(57) ABSTRACT

An oral care composition is described for use in the treatment or alleviation of the symptoms of dry mouth comprising polyvinyl pyrrolidone (PVP) or a derivative thereof, an anionic mucoadhesive polymer and an orally acceptable carrier or excipient.

1 Claim, No Drawings

COMPOSITION FOR XEROSTOMIA

This application is a §371 national phase entry of International Application No. PCT/EP05/08327, filed Jul. 29, 2005.

The present invention relates to mucoadhesive agent-containing compositions for oral use, such as toothpastes, sprays, mouthwashes, gels, lozenges, chewing gums, tablets, pastilles, instant powders, oral strips and buccal patches etc, and to the use of such compositions as an oral lubricant and to alleviate the discomfort associated with xerostomia.

Xerostomia, or dry mouth, is a condition in which an excessive dryness within the oral cavity occurs. Xerostomia is not itself a disease, but a symptom of various medical conditions, a side effect of radiation to the head and neck, or a side effect of a variety of medications. Xerostomia is a common complaint found often among older adults; however, does not appear to be related to age itself.

Xerostomia is often a contributing factor for both minor and serious health problems; it can affect nutrition and dental, as well as psychological health. Some common problems associated with xerostomia include a constant sore throat, burning sensations, difficulty speaking and swallowing, hoarseness and/or dry nasal passages. If left untreated, xerostomia decreases the oral pH and significantly increases the development of plaque and dental caries. Oral candidosis is one of the most common oral infections seen in association with xerostomia.

In view of the above, it would be advantageous to provide compositions for oral use as a lubricant to alleviate the discomfort associated with xerostomia.

U.S. Pat. No. 5,496,558, aims to address these problems with the provision of solid-form xerostomia products in the form of a lozenge, tablet, chewing gum and pastille, comprising a lubricating polymer, polyethylene glycol, an organic acid and sorbitol. U.S. Pat. No. 5,612,207 aims to address these problems with the provision of a lozenge comprising a hard candy base, a demulcent, a humectant and an organic acidulant.

However, there remains a need for alternative formulations with good mouth feel; that are able to lubricate and hydrate the mouth.

It has been found that the symptoms of dry mouth may be reduced by the use of an oral care composition comprising a combination of polyvinyl pyrrolidone (PVP) or a derivative thereof with an anionic mucoadhesive polymer.

A mucoadhesive polymer of the invention has an affinity for biological surfaces especially towards mucous membranes of the oral cavity. Mucoadhesive agents as used in the invention may be natural or synthetic.

Accordingly, the present invention provides a composition comprising PVP or a derivative thereof, an anionic mucoadhesive polymer and an orally acceptable carrier or excipient.

The compositions according to the present invention have good mouth coating, lubrication and mouth feel properties. Whilst compositions comprising an anionic mucoadhesive polymer are able to provide a good coating, they can suffer from negative sensory properties of being too tacky in use. This negative sensory property has surprisingly been overcome by the addition of PVP or a derivative thereof to an anionic mucoadhesive polymer.

Suitable derivatives of PVP include a vinyl pyrrolidone/vinyl acetate (VP/VA) copolymer or a vinyl pyrrolidone/vinyl alcohol (VP/VOH) copolymer. Preferably, compositions of the present invention comprise PVP or VP/VA copolymer Compositions of the present invention may suitably comprise from 0.1 to 20% w/w of PVP or a derivative thereof, preferably from, 0.5 to 10% w/w and more preferably 0.6 to 8% w/w.

The anionic mucoadhesive polymers useful in the present invention may be a cellulose gum, a saccharide gum or a polyacrylic acid polymer, or a mixture thereof.

Suitable cellulose gums include a carboxymethylcellulose (CMC) gum, for example sodium carboxymethylcellulose.

Suitable saccharide gums for use in the present invention include xanthan gum, guar gum, gum Arabic, tragacanth, gum karaya, locust bean gum and pectin or a mixture thereof. Xanthan gum is preferred.

Suitable polyacrylic acid polymers include carbomers, acrylate/$C_{10-30}$ alkyl acrylate cross polymers or polycarbophils available from Noveon Inc, 9911 Brecksville Road, Cleveland, Ohio 44141-3247. Preferred polyacrylic acids are carbomers or acrylate/$C_{10-30}$ alkyl acrylate cross polymers.

Suitably compositions of the present invention may comprise a combination of sodium carboxymethylcellulose and xanthan gum.

Suitably compositions of the present invention may comprise from 0.02 to 20% w/w of the anionic mucoadhesive polymer, preferably from 0.1 to 10% w/w, more preferably from 0.15 to 4% w/w, and most preferably from 0.2 to 2% w/w.

Suitably the compositions of the present invention may comprise PVP or a derivative thereof and an anionic mucoadhesive polymer in a weight ratio of from 5:1 to 1:1, preferably from 4:1 to 2:1.

"Compositions of the present invention may further comprise a silicon based oil, such as dimethicone or simethicone in an amount up to 8% w/w, eg from 1 to 5% w/w. The hydrophobic nature of the silicon based oil enhances the lubricity of the compositions in the oral cavity."

The oral compositions of the present invention are typically formulated in the form of toothpastes, sprays, mouthwashes, gels, lozenges (including centre filled lozenges), chewing gums, tablets, pastilles, instant powders, oral strips and buccal patches etc. Preferred compositions of the present invention are mouth sprays, mouthwashes and oral gels.

Known oral strips or buccal patches can be adapted to deliver the combination of polymers of the present invention to the oral cavity. For example a multilayered erodible film as disclosed in WO 03/015748 and U.S. Ser. No. 04/0062724 may incorporate PVP or a derivative thereof and an anionic mucoadhesive polymer of the present invention either in the adhesive first layer and/or the erodible second layer as disclosed therein. If desired a silicon based oil can be used alone or with other hydrophobic polymers to be incorporated into or to coat the erodible layer as disclosed therein.

Suitable orally acceptable carriers and excipients include abrasive polishing materials (especially for a dentifrice), flavouring agents, humectants, binders, sweetening agents, surfactants, preservatives, buffering agents, colouring agents and water.

Suitable humectants for use in compositions of the invention include glycerine, sorbitol, xylitol, propylene glycol or polyethylene glycol, or mixtures thereof; which humectant may be present in the range from 5 to 70%.

Suitable flavouring agents for use in the present invention include peppermint, spearmint, and fruit flavours. Flavouring agents provide an additional benefit in stimulating salivary flow, which helps alleviate the symptoms of dry mouth. If desired, additional salivary stimulants can be included such as edible organic acids, e.g. citric acid.

Suitable preservatives for use in the invention include parabens (methyl and propyl parabens), sodium benzoate, and potassium sorbate.

Suitable buffering agents for use in the invention include phosphate buffers such as disodium phosphate, sodium phosphate or citrate buffers.

"Suitable surfactants for use in the invention include polyethyleneglycols (PEG), hydrogenated caster oils, sorbitan esters, polyethylene-polypropylene tri-block copolymers (such as Poloxamers™). Preferred surfactants include PEG-40® or PEG-60® hydrogenated castor oil and sorbitan esters."

Additional ingredients suitable for use in the invention include remineralising agents, antimicrobial agents, anti-caries agents, anticalculus agents, moisturising agents, breath freshening agents and desensitising agents.

Suitable antimicrobial agents for use in the invention include chlorhexidine, cetylpyridinium chloride, zinc salts or triclosan. Preferred antimicrobial agents are cetylpyridinium chloride, chlorhexidine and zinc salts.

"Suitable anti-caries agents for use in the invention include a source of fluoride ions such as an alkali metal salt, for example sodium fluoride, or sodium monofluorophosphate, tin (II) fluoride or an amine fluoride salt such as OLAFLUR® or DECAFLUR®. Suitably the composition will comprise between 1 and 2500 ppm of fluoride ions."

Compositions according to the present invention may be prepared by admixing the ingredients in the appropriate relative amounts in any order that is convenient and thereafter and if necessary including a buffering agent to adjust the pH to give the final desired value.

The compositions according to the present invention will have a pH which is orally acceptable, typically ranging from about pH 5 to 10 and more preferable pH 5.5 to 8.

Mouthwash and mouth spray compositions may be provided in a "ready to use" form; as a concentrated solution, for dilution by the user immediately prior to use; or in solid form, such as a tablet or as instant powder in a sachet, for dissolution by the user immediately prior to use. Tablets may suitably be prepared using xylitol and/or sorbitol as the major ingredient. The sachets and tablets may be formulated to provide, on dissolution, a still mouthwash, or, by the incorporation of a suitable effervescent couple, for instance sodium carbonate/bicarbonate and citric acid, an effervescent mouthwash.

The compositions of the present invention are of use in alleviating the symptoms of xerostomia. In particular they are of use in lubricating and hydrating the oral cavity.

The present invention also provides a method for treating xerostomia in a human or animal, wherein said method comprises administration of a therapeutically effective amount of a composition as hereinbefore described.

The present invention is illustrated by the following examples but is not limited thereby.

EXAMPLE 1

Mouth Spray 1

| Ingredient | Amount % w/w |
| --- | --- |
| Water | 52.940 |
| Glycerin | 35.000 |
| Xylitol | 7.500 |
| VP/VA copolymer | 1.000 |
| PEG 60 Hydrogenated castor oil | 1.600 |

-continued

| Ingredient | Amount % w/w |
| --- | --- |
| Flavour ingredients | 0.810 |
| Sodium benzoate | 0.500 |
| Xanthan gum | 0.400 |
| Methylparaben | 0.100 |
| Propylparaben | 0.100 |
| Cetylpyridinium chloride | 0.050 |

EXAMPLE 2

Mouth Spray 2

| Ingredient | Amount % w/w |
| --- | --- |
| Water | 51.750 |
| Glycerin | 35.000 |
| Xylitol | 7.500 |
| PVP | 2.640 |
| PEG 60 Hydrogenated castor oil | 0.850 |
| Flavour ingredients | 0.810 |
| Sodium benzoate | 0.500 |
| Xanthan gum | 0.400 |
| Cellulose gum | 0.400 |
| *Aloe Barbadensis* | 0.100 |
| Cetylpyridinium chloride | 0.050 |

EXAMPLE 3

Mouthwash

| Ingredient | Amount % w/w |
| --- | --- |
| Water | 84.214 |
| Glycerin | 7.000 |
| Sorbitol | 5.000 |
| Poloxamer 338 | 1.000 |
| PEG 60 Hydrogenated castor oil | 1.000 |
| VP/VA copolymer | 0.750 |
| Sodium benzoate | 0.500 |
| Cellulose gum | 0.200 |
| Flavour ingredients | 0.120 |
| Cetylpyridinium chloride | 0.050 |
| Methyl paraben | 0.050 |
| Propyl paraben | 0.050 |
| Sodium saccharin | 0.050 |
| Xanthan gum | 0.010 |
| Disodium phosphate | 0.003 |
| Sodium phosphate | 0.002 |
| FD&C Blue No. 1 | 0.001 |

EXAMPLE 4

Oral Gel

| Ingredient | Amount % w/w |
| --- | --- |
| PVP | 8.000 |
| Cellulose | 1.000 |
| Carbomer | 1.000 |
| Sorbitol | 25.000 |
| Xylitol | 10.000 |
| Glycerin | 19.000 |

-continued

| Ingredient | Amount % w/w |
|---|---|
| Flavour ingredients | 0.100 |
| FD&C Blue No. 1 (1% solution) | 0.400 |
| Water | 35.500 |

EXAMPLE 5

Sensory Evaluation

Sensory evaluation for the optimisation of polymers for use in xerostomia applications was performed using small scale panel testing. Sensory findings include:

The use of CMC alone at a level which provides good mouth coating produced sensory negatives of 'tacky' and 'gloopy'.

Sensory testing of Xanthan gum alone, at levels which provided good mouth coating, produced negative sensory feedback of 'gloopy' and comments of tackiness A blend of CMC, Xanthan gum and PVP was found to deliver good coating with a smooth, good mouthfeel and the ability to lubricate and hydrate the mouth. This polymer combination was tested alongside a CMC, Xanthan, Dimethicone combination. Substitution of the PVP for Dimethicone reduced the coating benefit and smoothness of the polymer blend.

The sensory negatives associated with the use of CMC or Xanthan alone, which deliver coating and mucoadhesion benefits, have been overcome by the incorporation of PVP in a combination of CMC and xanthan gum, this effect is further suggested by the loss of smoothness when PVP was substituted in the blend for an alternative polymer resulting in the loss of all smooth type comments.

EXAMPLE 6

Sensory Evaluation

Further sensory evaluation for the optimisation of polymers for use in xerostomia applications was performed using small scale panel test consisting of six panelists.

Panellists tested 10 ml of polymer solutions as shown in the table below:

| Polymer Solution | CMC % w/w | Xanthan % w/w | PVP % w/w |
|---|---|---|---|
| Xanthan | | 1.0 | |
| Xanthan + PVP | | 1.0 | 2.5 |
| CMC | 1.0 | | |
| CMC + PVP | 1.0 | | 2.5 |
| Xanthan + CMC | 0.75 | 0.25 | |
| Xanthan + CMC + PVP | 0.75 | 0.25 | 2.5 |

Sensory findings include:

CMC/CMC+PVP Solutions

Addition of PVP to a CMC solution improved the organoleptic characteristics of the polymer solutions. PVP significantly ($p=0.01$) reduced the tackiness of the CMC solution and provided a smoother oral texture. The mouthfeel and aftertaste of the CMC+PVP solution was more pleasant. The mouth was more moisturised. Both polymer solutions were perceived to be moderately gloopy. There was a trend for the CMC+PVP solution to be perceived as being more viscous and gel like (more gloopy) than the CMC solution. This is explained by the fact that there is more overall polymer increasing the viscosity of the solution.

Xanthan/Xanthan+PVP

In this small scale panel testing no significant difference was observed between the organoleptic characteristics of a xanthan solution and a mixture of xanthan and PVP. There was a trend that the addition of PVP to xanthan solution slightly reduced the pleasantness of the mouth feel and the smoothness of the oral texture of the solution owing to an increased gloopy sensation, which can be explained by the increase in overall polymer in the system. However, adding PVP increased the ability to coat the mouth. Both polymers solutions were perceived leaving the mouth moderately moisturised and lubricated. Importantly the addition of PVP reduced the tackiness of the xanthan solution.

Xanthan+CMC/Xanthan+CMC+PVP

Addition of PVP to a xanthan+CMC solution improved significantly ($p=0.03$) the smoothness of the oral texture of the solution. There was a trend for PVP to reduce tackiness of the xanthan+CMC solution and to provide a more pleasant mouthfeel and to leave the mouth moisturised and lubricated. Xanthan+CMC+PVP solution was perceived to be more gloopy in view of the fact that there was more overall polymer increasing the viscosity of the solution.

The invention claimed is:

1. A liquid composition comprising:
   52.94% by weight of water;
   35% by weight of glycerin;
   7.5% by weight of xylitol;
   1% by weight of vinyl-pyrolidone/vinyl acetate copolymer;
   1.6% by weight of polyethylene glycol hydrogenated castor oil;
   0.4% by weight of xanthan gum; and
   one or more preservatives, antimicrobials, and flavoring agents
   wherein said composition is in the form of a liquid mouthwash or mouth spray solution and is exclusive of an anticalculus agent and abrasive.

* * * * *